United States Patent [19]

Price

[11] Patent Number: 5,538,863
[45] Date of Patent: Jul. 23, 1996

[54] EXPRESSION SYSTEM COMPRISING MUTANT YEAST STRAIN AND EXPRESSION VECTOR ENCODING SYNTHETIC SIGNAL PEPTIDE

[75] Inventor: Virginia L. Price, Seattle, Wash.

[73] Assignee: Immunex Corporation, Seattle, Wash.

[21] Appl. No.: 86,335

[22] Filed: Jul. 1, 1993

[51] Int. Cl.$^6$ .............................. C12N 1/19; C12N 15/81; C12P 21/02
[52] U.S. Cl. ................ 435/69.1; 435/254.2; 435/254.21; 435/320.1; 536/23.1; 536/23.4; 536/23.7; 536/24.1
[58] Field of Search ................................ 435/69.1, 69.4, 435/69.5, 69.52, 69.7, 69.8, 69.9, 71.1, 171, 172.3, 243, 254.1, 254.2, 254.21, 255.1, 255.2, 320.1; 536/23.1, 23.4, 23.5, 23.51, 23.7, 24.1

[56] References Cited

U.S. PATENT DOCUMENTS

| | | | |
|---|---|---|---|
| 4,546,082 | 10/1985 | Kurjan et al. | 435/172.3 |
| 4,775,622 | 10/1988 | Hitzeman et al. | 435/69.4 |
| 5,010,003 | 4/1991 | Chang et al. | 435/69.9 |
| 5,073,627 | 12/1991 | Curtis et al. | 530/351 |
| 5,081,228 | 1/1992 | Dower et al. | 530/351 |
| 5,162,498 | 11/1992 | Christiansen | 530/324 |

FOREIGN PATENT DOCUMENTS

| | | |
|---|---|---|
| 0123544A2 | 10/1984 | European Pat. Off. . |
| 201208 | 11/1986 | European Pat. Off. . |
| 0324274A1 | 7/1989 | European Pat. Off. . |
| 0329127B1 | 8/1989 | European Pat. Off. . |
| 0460846A1 | 12/1991 | European Pat. Off. . |
| WO92/11378 | 7/1992 | WIPO . |

OTHER PUBLICATIONS

Achstetter, Tilman et al., *Gene* 110:25–31; 1992.
Kikuchi, Masakazu et al., *TIBTECH* 9:208–211; 1991.
Hofmann, Kathryn J. et al., *Gene* 101:105–111; 1991.
Rose, M., et al., *Methods in Yeast Genetics, A Laboratory Course Manual*, Cold Spring Harbor Press, Cold Spring Harbor, N.Y., 11–17; 1990.
Sleep, D. et al., *Bio/Technology* 8:42–46; 1990.
Sato, Takaaki et al., *Gene* 83:355–365; 1989.
Waters, M. Gerard et al., *The Journal of Biological Chemistry* 263:6209–6214; 1988.
Piggot, J. R. et al., *Current Genetics* 12:561–567; 1987.
Yamamoto, Yoshio et al., *Biochemical and Biophysical Research Communications* 149:431–436; 1987.
Kaiser, Chris A. et al., *Science* 235:312–317; 1987.
von Heijne, Gunnar, *Journal of Molecular Biology* 184:99–105; 1985.
*Catalogue Yeast Genetic Stock Center*, Fifth Ed., Univ. of California, Berkeley, CA, 1984.
Perlman, Daniel et al., *Journal of Molecular Biology* 167:391–409; 1983.
von Heijne, Gunnar, *European Journal of Biochemistry* 133:17–21; 1983.
Mercier, J–C. et al., *Annals New York Academy of Sciences* 232–251; 1980.
Schechter, I. et al., *Annals New York Academy of Sciences* 218–231; 1980.

*Primary Examiner*—Mindy Fleisher
*Assistant Examiner*—Philip W. Carter
*Attorney, Agent, or Firm*—Kathryn A. Anderson

[57] ABSTRACT

A novel strain of *Saccharomyces cerevisiae* is useful as a host cell in the production of recombinant proteins. The novel *S. cerevisiae* cells transformed with a recombinant expression vector encoding a desired heterologous protein, preferably fused to a suitable N-terminal signal peptide, are cultivated under conditions that promote expression of the protein. Also provided are signal peptides derived by replacing the native signal peptidase cleavage site of a type I interleukin-1 receptor signal peptide with the tripeptide AlaXAla, wherein X represents an amino acid selected from Leu, Phe, and Gln. An expression system comprises a yeast host cell (preferably the novel *S. cerevisiae* strain) transformed with an expression vector comprising a promoter functional in yeast cells operably linked to DNA encoding the novel signal peptide, which is fused to the N-terminus of DNA encoding a desired heterologous protein.

25 Claims, 3 Drawing Sheets

1

EXPRESSION SYSTEM COMPRISING MUTANT YEAST STRAIN AND EXPRESSION VECTOR ENCODING SYNTHETIC SIGNAL PEPTIDE

BACKGROUND OF THE INVENTION

Yeast cells are among the cell types that have been employed as host cells in the production of heterologous proteins through recombinant DNA technology. Secretion of the desired protein from the yeast cells is generally advantageous for reasons that include facilitating the purification process, since the desired protein is recovered from the culture supernatant rather than from the complex mixture of proteins that results when yeast cells are disrupted to release intracellular proteins. Secretion also reduces the deleterious (e.g., toxic) effect that intracellular accumulation of a given foreign protein may have on the host cell.

Secreted proteins generally are initially expressed as precursors bearing an N-terminal signal or leader peptide. Signal peptides generally contain a positively charged N-terminus followed by a hydrophobic core, followed by a recognition site for an enzyme known as signal peptidase. This enzyme cleaves the signal peptide from the protein during translocation. The protein is transported from the endoplasmic reticulum to the Golgi apparatus, and then follows one of a number of routes in the secretory pathway, depending on the nature of the protein. The protein may be secreted into the culture medium or may be retained on the cell surface, for example. Certain receptors that comprise extracellular, transmembrane, and cytoplasmic domains are examples of proteins that may be retained on the cell membrane, with only the extracellular domain located outside the cell.

The leader sequences of certain secreted proteins comprise peptides that are located C-terminal to the signal peptide and are processed from the mature protein of interest subsequent to cleavage of the signal peptide. Such leaders often are referred to as prepro peptides, wherein the pre region is the signal sequence and the pro region designates the remainder of the leader. One example is the yeast α-factor leader, which contains a signal peptide (including a C-terminal signal peptidase recognition site AlaLeuAla) followed by a pro region containing a basic amino acid pair LysArg that constitutes a KEX2 protease processing site, immediately followed by a peptide GluAlaGluAla (SEQ ID No:7) at the C-terminus of the pro region. Processing of this leader involves removal of the signal peptide by signal peptidase, followed by cleavage between the Lys and Arg residues by KEX2 protease. The GluAlaGluAla (SEQ ID No:7) residues are subsequently removed by a peptidase that is the product of the STE13 gene (Julius et al., *Cell* 32:839, 1983). The yeast α-factor leader is described in U.S. Pat. No. 4,546,082.

Signal peptides derived from proteins naturally secreted by yeast cells have been employed in recombinant expression systems for production of heterologous proteins in yeast. The use of mammalian signal peptides in yeast expression systems also has been reported, although certain of the mammalian signal peptides were not effective in promoting secretion of heterologous proteins in yeast.

Research continues to be directed toward increasing the levels of secreted and correctly processed recombinant proteins produced in yeast expression systems. Such improved expression systems would provide advantages such as the cost savings afforded by more efficient production and purification processes, and the time savings realized by researchers when protein purification is simplified through efficient secretion of the desired protein from the cell. A need remains for alternative and improved expression systems for producing recombinant proteins in yeast. This goal may be pursued by isolating new yeast strains having advantageous properties, or by developing new expression vectors.

SUMMARY OF THE INVENTION

A novel mutant strain of *Saccharomyces cerevisiae* has been isolated and found to be useful in expression systems for production of recombinant proteins. The mutant yeast cells are transformed with an expression vector comprising a DNA sequence encoding a heterologous protein, operably linked to regulatory sequences suitable for expression of said protein in the yeast strain. The expression vector advantageously comprises DNA encoding a suitable signal or leader peptide fused to the 5' end of the DNA encoding the heterologous protein, to effect secretion of the heterologous protein from the cell. The transformed cells are cultivated to allow expression of the desired protein, which is recovered from the culture supernatant.

Also provided by the present invention is an expression vector useful for expression and secretion of recombinant proteins in yeast cells, preferably in the mutant *S. cerevisiae* strain. The expression vector comprises a yeast promoter operably linked to a DNA sequence encoding a novel signal peptide derived from a type I interleukin-1 receptor signal sequence lacking its native signal peptidase recognition site. The novel signal peptide preferably comprises an amino acid sequence selected from the group consisting of:

| | |
|---|---|
| MetLysValLeuLeuGlyLeuIleCysLeuMetVal[Pro]$_m$[Z]$_n$AlaXAla, | (SEQ ID NO: 1) |
| MetGluAsnMetLysValLeuLeuGlyLeuIleCysLeuMetVal[Pro]$_m$[[Z]$_n$AlaXAla, and | (SEQ ID NO: 2) |
| MetLysValLeuLeuArgLeuIleCysPheIleAlaLeuLeu[Z]$_n$AlaXAla, | (SEQ ID NO: 5) | wherein:

m is 0 or 1,

Z represents a spacer peptide comprising from 1–5 amino acids, preferably from 1–3 amino acids;

n is 0 or 1, and

X is an amino acid selected from the group consisting of Leu, Phe, and Gln.

The AlaXAla tripeptide replaces the native signal peptidase recognition site of the interleukin-1 receptor signal sequences. The novel signal peptides and DNA encoding said signal peptides are encompassed by the present invention.

DNA encoding a desired heterologous protein is inserted into the expression vector such that it is fused to the 3' end of the DNA segment encoding the signal peptide. Yeast cells transformed with the resulting expression vector are cultivated to express and secrete the desired protein, which is recovered from the culture supernatant.

DETAILED DESCRIPTION OF THE INVENTION

Figure 1:
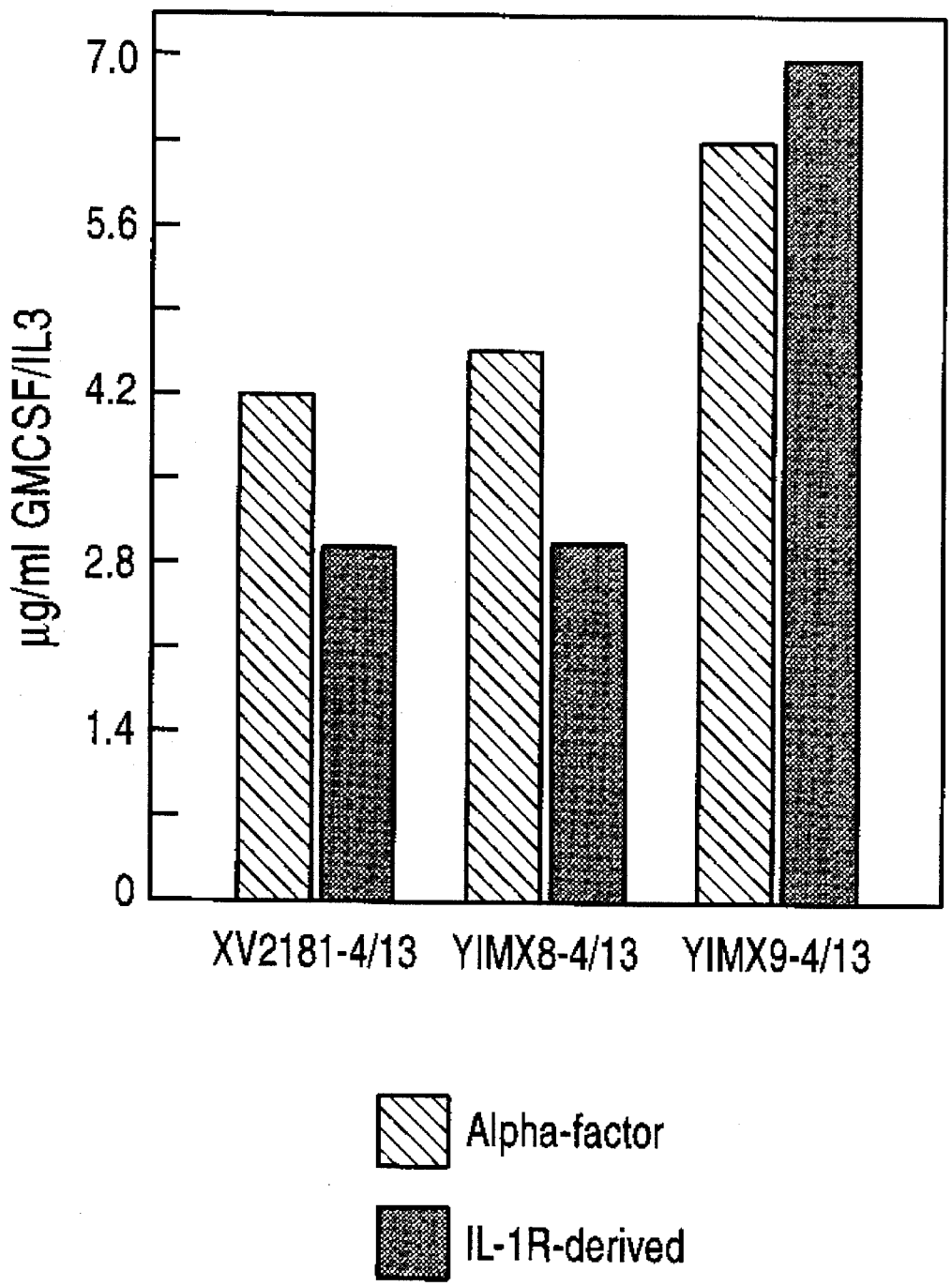
FIG. 1 presents the results of the experiment described in example 2, in which levels of secretion of a heterologous fusion protein were compared for three yeast strains (including the novel mutant yeast strain designated YIMX9) transformed with two different expression vectors. One of the vectors, pIXY654, is an expression vector of the present invention, encoding a novel signal peptide.

A novel strain of *Saccharomyces cerevisiae* designated YIMX9 has been isolated and found to be useful as a host strain for production of heterologous proteins using recombinant DNA technology. This novel strain of the present invention was derived by mutation as described in example 1 below, and has been deposited with the American Type Culture Collection as ATCC 74224.

The present invention also provides yeast strain ATCC 74224 cells transformed with an expression vector that comprises a promoter functional in the yeast cells, operably linked to a DNA encoding a heterologous protein. Expression vectors conventionally used to express recombinant proteins in *S. cerevisiae* may be employed, examples of which are described below.

The expression vector advantageously comprises DNA encoding a suitable leader or signal peptide fused to the 5' end of the DNA encoding the heterologous protein. The leader peptide thus is fused to the N-terminus of the heterologous protein when initially expressed, and promotes secretion of the expressed heterologous protein from the cell. The leader peptide is cleaved by specific intracellular protease(s) during secretion, so that the heterologous protein recovered from the culture medium does not have the leader peptide attached thereto.

Any signal or leader peptide recognized by *S. cerevisiae* cells may be employed. Examples are the leader or signal peptide of such proteins as the *S. cerevisiae* αfactor MFα1 (described in U.S. Pat. No. 4,546,082), *S. cerevisiae* invertase, encoded by the SUC2 gene (Smith et al., *Science* 229:1219, 1985; Chang et al., *Mol. Cell. Biol.* 6:1812, 1986), *S. cerevisiae* acid phosphatase, encoded by PH05 (Smith et al., 1985, supra; Hinnen et al. in Korhola and Vaisanen, Eds., *Gene Expression in Yeast, Foundation for Biotechnological and Industrial Fermentation Research*, Vol. 1, Kauppakirjapaino Oy, Helsinki, 1983, pp. 157–163), *S. carlsbergensis* α-galactosidase (the MEL1 gene product) (Hofmann and Schultz, *Gene* 101:105, 1991), *K. lactis* killer toxin (ORF2) (Stark and Boyd, *EMBO J.* 5:1995, 1986; Baldari et al., *EMBO J.* 6:229, 1987), *S. cerevisiae* killer toxin (Tokunaga et al., *Nuc. Acids res.* 16:7499, 1988), and the *S. cerevisiae* BGL2 gene product (Achstetter et al., *Gene* 110:25, 1992). The pre or prepro region of a given leader (discussed above) may be employed.

In one embodiment of the present invention, a novel signal peptide, derived by replacing the native signal peptidase recognition site of a mammalian signal peptide with the tripeptide AlaXAla, is employed. X represents an amino acid selected from Leu, Phe, and Gln, with Leu being preferred. The last (i.e., C-terminal) three amino acid of signal peptides (i.e., the amino acids at the positions conventionally designated −3, −2, and −1) are generally considered to constitute the recognition site for the signal peptidase enzyme, with cleavage occurring immediately after the amino acid at position −1 (last amino acid of the signal peptide). Deletion of the amino acids at positions −3 through −1 or −4 through −1 (i.e., the C-terminal three or four amino acids) of a native signal peptide is sufficient to disrupt the signal peptidase recognition site. The novel, modified signal peptide may additionally include spacer amino acids (e.g., encoded by a linker employed to add a restriction site) positioned between the truncated native signal peptide sequence and the AlaXAla sequence.

In one embodiment of the invention, an expression vector comprises a yeast promoter operably linked to a DNA sequence encoding a novel signal peptide of the formula sig $[Z]_n$ AlaXAla, wherein:

sig represents a truncated type I interleukin-1 receptor signal sequence lacking the amino acids at positions y through −1 of the native signal sequence, wherein y is −3 or −4;

Z represents a spacer peptide comprising from 1–5 amino acids, preferably 1–3 amino acids;

n is 0 or 1; and

X is an amino acid selected from the group consisting of Leu, Phe, and Gln.

The AlaXAla tripeptide replaces the native signal peptidase recognition site. X is preferably Leu.

The optional spacer peptide Z contains from 1 to 5 amino acids, preferably from 1 to 3 amino acids. Z contains neither the native signal peptidase recognition site of the interleukin-1 receptor signal sequence, nor a tripeptide of the formula AlaXAla. One example of Z is a peptide encoded by a linker useful for constructing a recombinant vector, e.g., a linker containing a desired restriction site.

For expression of a desired heterologous protein, DNA encoding the protein is fused to the 3' end of the DNA segment encoding the signal peptide. The term "heterologous protein" as used herein indicates that the protein to be expressed is not naturally expressed in the yeast host cell. Examples of such heterologous proteins are presented below.

The sig moiety is derived from the signal sequence of a type I interleukin-1 receptor. Such signal sequences include the human and murine type I IL-1 receptor signal sequences described in U.S. Pat. No. 5,081,228 (hereby incorporated by reference) or homologous signal peptides derived from other mammalian species.

The amino acid sequence of the native signal peptide of murine type I IL-1R is:

<u>Met</u>GluAsn<u>Met</u>LysValLeuLeuGlyLeuIleCysLeuMetValProLeuLeuSer  (SEQ ID NO: 8)

wherein the two alternative initiator methionine residues are underlined. The native DNA sequence encoding this signal peptide is:

<u>ATG</u> GAG AAT <u>ATG</u> AAA GTG CTA CTG GGG CTC ATT TGT CTC ATG GTG CCT CTG CTG TCG  (SEQ ID NO: 9)

The amino acid sequence of the native human type I IL-1R signal peptide is:

MetLysValLeuLeuArgLeuIle-CysPheIleAlaLeuLeuIleSerSer (SEQ ID NO: 10)

and the native DNA sequence encoding this signal peptide is:

ATG AAA GTG TTA CTC AGA CTT ATT TGT TTC ATA GCT CTA CTG ATT TCT TCT.  (SEQ ID NO: 11)

Novel signal peptides of the present invention include but are not limited to those of the formula:

MetLysValLeuLeuGlyLeuIleCysLeuMetVal[Pro]$_m$[Z]$_n$AlaXAla  (SEQ ID. NO: 1)

or

MetGluAsnMetLysValLeuLeuGlyLeuIleCysLeuMetVal[Pro]$_m$[Z]$_n$AlaXAla  (SEQ ID NO: 2)

wherein the underlined segments are N-terminal fragments of the above-described murine type I IL-1R signal sequence, m is 0 or 1, and symbols Z, n, and X are as described above. The underlined segments are the sig moiety, and constitute the murine type I IL-1R signal sequence from which the last three amino acids constituting the signal peptidase recognition site have been deleted. The Pro residue at the −4 position also may be deleted. The second formula comprises the three additional N-terminal amino acids encoded when translation is initiated at the first of the two alternative initiation codons, as described above.

Particularly preferred signal peptides of the present invention are:

<u>MetLysValLeuLeuGlyLeuIleCysLeuMetVal</u><u><u>LeuGlyThr</u></u>AlaLeuAla  (SEQ ID NO: 3)

and

MetGluAsn<u>MetLysValLeuLeuGlyLeuIleCysLeuMetVal</u><u><u>LeuGlyThr</u></u>AlaLeuAla  (SEQ ID NO: 4)

wherein the AlaLeuAla moiety constitutes a recognition site for signal peptidase. The underlined segment is the murine type I IL-1R signal sequence lacking the last four amino acids thereof. The double-underlined segment is a spacer peptide Z that is encoded by a linker containing a restriction site, as described in example 2.

Another signal peptide of the present invention comprises the following amino acid sequence:

(SEQ ID NO: 5)

<u>MetLysValLeuLeuArgLeuIleCysPheIleAlaLeuLeu</u>[Z]$_n$AlaXAla wherein the underlined segment is the human type I IL-1R signal peptide lacking the signal peptidase recognition site thereof (amino acids −3 through −1), and X and [Z]$_n$ are as defined above. In one embodiment (SEQ ID NO: 6), Z is the tripeptide spacer LeuGlyThr (as for the modified murine IL-1R signal peptides above) and X is Leu.

Expression vectors

The present invention provides the foregoing novel signal peptides and isolated DNA sequences encoding the novel signal peptides. Also provided are expression vectors comprising a promoter sequence functional in yeast cells that is operably linked to said DNA encoding a novel signal peptide; expression vectors that additionally comprise a DNA sequence encoding a desired heterologous protein fused to the 3' end of the DNA encoding the signal peptide; and yeast cells transformed with the expression vectors.

The expression vectors encoding a novel signal peptide of the present invention are useful for expressing heterologous proteins in yeast host cells. The heterologous protein is secreted from the yeast cells, thus facilitating purification of the desired recombinant protein. Yeast cells that may be transformed with the inventive vectors include, but are not limited to, yeast of the genera Saccharomyces (e.g., *S. cerevisiae*), Pichia, or Kluyveromyces (e.g., *K. lactis*). Preferably, the mutant yeast strain YIMX9 deposited with the American Type Culture collection as ATCC 74224 is employed as the host strain.

*S. cerevisiae* strain YIMX9 is useful as a host cell for the novel expression vectors of the present invention and for conventional expression vectors employed to express recombinant proteins in yeast. Expression vectors for use with various types of host cells, including yeast cells, are described, for example, in Pouwels et al. *Cloning Vectors: A Laboratory Manual*, Elsevier, N.Y., (1985).

Appropriate expression vectors comprise regulatory sequence(s) suitable for expression of DNA encoding a desired heterologous protein in a yeast host cell. Examples of regulatory sequences include promotors, operators, and enhancers, ribosomal binding sites, and sequences that control transcription and translation initiation and termination. The regulatory sequences are operably linked to the DNA sequence to be expressed. For example, a promotor sequence is said to be operably linked to a coding sequence (e.g., DNA encoding a signal peptide fused to a desired heterologous protein) if the promotor controls the transcription of the coding sequence.

The expression vector comprises a yeast promoter in that it contains a DNA sequence that functions as a promoter for gene transcription in yeast cells. Any suitable yeast promoter sequence may be employed. Suitable promoter sequences for yeast vectors include promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968, and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. The ADH2 promoter has been described by Russell et al. (*J. Biol. Chem.* 258:2674, 1982) and Beier et al. (*Nature*300:724, 1982). Other suitable vectors and promoters for use in yeast expression are further described in Hitzeman, EP 73,657.

Expression vectors generally comprise one or more phenotypic selectable markers (e.g., a gene encoding a protein that confers antibiotic resistance or that supplies an autotrophic requirement) and an origin of replication recognized by the intended host cell to ensure amplification within the host. Yeast vectors commonly contain an origin of replication from a 2 µ yeast plasmid, an autonomously replicating sequence (ARS), a promoter region, sequences for polyadenylation, sequences for transcription termination, and a selectable marker.

Shuttle vectors replicable in more than one type of cell (wherein one of the cell types is yeast) also may be employed. Such vectors comprise multiple origins of replication and selective markers, allowing manipulations such as recombinant vector construction and cloning in one cell type, e.g., a prokaryotic cell type, and expression of recombinant protein in yeast. For example, a shuttle vector that replicates in both yeast and *E. coli* and functions as an expression vector in yeast may comprise DNA sequences from a prokaryotic vector for selection and replication in *E. coli*, and yeast-derived sequences such as a glucose-repressible ADH2 promoter, an origin of replication from a 2 µ yeast plasmid, and an α-factor leader sequence. Such a shuttle vector may employ elements derived from a commercially available plasmid such as the prokaryotic cloning vector pBR322 (ATCC 37017). pBR322 contains an origin of replication functional in *E. coli* as well as genes for ampicillin and tetracycline resistance and thus provides simple means for identifying transformed cells.

A DNA segment encoding a novel signal peptide of the present invention may be prepared and inserted into a yeast expression vector by conventional techniques. Oligonucleotide(s) encoding the desired novel signal peptide may be chemically synthesized by standard techniques, for example. This use of oligonucleotides is illustrated for one embodiment of the invention in example 2. Restriction sites are useful for excising and inserting alternative oligonucleotides into the expression vector constructed as described in example 2 (e.g., to vary the AlaXAla moiety).

The present invention thus provides a method for production of recombinant proteins, comprising cultivating *S. cerevisiae* strain ATCC 74224 cells transformed with an expression vector as described above (an inventive or conventional expression vector), under conditions suitable for expression of the heterologous protein encoded by the vector. The expressed protein is recovered from the cell culture (from the culture medium if the vector comprises a signal peptide).

Also provided herein is a method for producing a recombinant protein, comprising cultivating a yeast cell (e.g., of the genera Saccharomyces, Pichia, or Kluyveromyces, preferably *S. cerevisiae* ATCC 74224) transformed with an expression vector of the present invention under conditions suitable for expression of the heterologous protein encoded by the vector. The expressed protein is recovered from the culture medium.

Heterologous protein

The heterologous protein encoded by the expression vectors may be any protein or polypeptide that is heterologous to (i.e., not naturally produced in) the yeast host cells, and for which production via recombinant DNA technology is desired. Such proteins include, but are not limited to, proteins having use in the medical or scientific research fields.

In one embodiment of the invention, the heterologous protein is a mammalian cytokine. The term "cytokines" encompasses a diverse group of soluble proteins that are released by one type of cell and mediate a biological effect on another cell type. Biological activities exhibited by cytokines include control of proliferation, growth, and differentiation of various cell types, among which are cells of the hematopoietic or immune systems.

Examples of cytokines include the interleukins (e.g., interleukins 1 through 12), the interferons (IFNα, IFNβ, and IFNγ), tumor necrosis factor (TNFα and TNFβ), epidermal growth factor (EGF), platelet-derived growth factor (PDGF), leukemia inhibitory factor (LIF), colony stimulating factors, and fusion proteins comprising two or more cytokines. Examples of colony stimulating factors (CSF), which control growth and differentiation of hematopoietic cells, are granulocyte-CSF (G-CSF), granulocyte-macrophage-CSF (GM-CSF), macrophage-CSF (M-CSF or CSF-1), mast cell growth factor (MGF), and erythropoietin (EPO). An example of a fusion protein comprising multiple cytokines is the fusion protein comprising IL-3 and GM-CSF described in U.S. Pat. No. 5,073,627.

The biological activity of cytokines generally is mediated by binding of the cytokine to a receptor specific for that cytokine, located on the surface of target cells. A number of such cytokine receptor proteins have been isolated and characterized. Soluble forms of certain receptors have been purified, including naturally occurring or recombinant soluble receptor proteins, e.g, comprising only the extracellular domain of the receptor. Two or more copies of the same or different receptors may be expressed as a fusion protein in recombinant systems.

One family of cytokine receptors includes two different TNF receptors (Type I and Type II) (Schall et al., *Cell* 61:361, 1990, and Smith et al., *Science* 248:1019, 1990); nerve growth factor receptor (Johnson et al., *Cell* 47:545, 1986); B cell antigen CD40 (Stamenkovic et al., *EMBO J.* 8:1403, 1989); T cell antigen OX40 (Mallett et al., *EMBO J.* 9:1063, 1990); human Fas antigen (Itoh et al., *Cell* 66:233, 1991); and murine receptor 4-1BB (Kwon et al., *Cell. Immunol.* 121:414, 1989, and Kwon et al., *Proc. Natl. Acad. Sci. USA* 86:1963, 1989). Interleukin receptors that have been identified include, but are not limited to, type I IL-1 receptor (U.S. Pat. No. 5,081,228); type II IL-1 receptor (WO91/18982); IL-2 receptor (EP 162,699); IL-4 receptor (EP 367,566); and IL-7 receptor (U.S. Pat. No. 5,194,375).

The above-described cytokines and cytokine receptors are among the heterologous proteins that may be produced in accordance with the methods of the present invention, as are other growth factors (including T-cell growth factors), cell surface antigens including tyrosine kinases, and their cognate receptors. In particular embodiments of the invention, the heterologous protein is a colony stimulating factor, a fusion protein comprising IL-3 and a colony stimulating factor, a tumor necrosis factor receptor, a T-cell growth factor derived from epithelial cells, an interleukin, or an interleukin receptor. Particularly preferred heterologous proteins include IL-1R, IL-4R, IL-7R, type II TNF-R, GM-CSF, and the fusion proteins comprising IL-3 and GM-CSF described in U.S. Pat. No. 5,073,627.

The heterologous protein may be a native form of the protein; a truncated or variant form thereof that retains the desired biological activity; or a fusion protein, for example.

Soluble polypeptides derived from the extracellular domain of a cell surface protein are included. Naturally occurring variants include those resulting from alternative mRNA splicing events or proteolytic cleavage. One can link multiple copies of a desired protein, or two different proteins, via peptide linkers using recombinant DNA technology. The production of recombinant fusion proteins comprising peptide linkers is illustrated in U.S. Pat. No. 5,073,627, for example.

Variant forms of a protein comprise an amino acid sequence that differs from the native amino acid sequence by one or a plurality of substitutions, deletions, or additions, but retain a desired biological activity. Such variants can be produced using conventional in vitro mutagenesis techniques to introduce desired mutations into a DNA encoding the protein of interest. A variant amino acid sequence may comprise conservative amino acid substitution(s), for example.

Variant heterologous proteins comprising inactivated N-glycosylation sites are within the scope of the present invention. Such variants are expressed in a more homogeneous, reduced carbohydrate form. N-glycosylation sites in eukaryotic polypeptides are characterized by an amino acid triplet Asn-X-Y, wherein X is any amino acid except Pro and Y is Ser or Thr. In this sequence, carbohydrate residues are covalently attached at the Asn side chain. Addition, substitution, or deletion of residue(s) so that the Asn-X-Y triplet is no longer present inactivates the site. In one embodiment, a conservative amino acid substitution replaces the Asn residue, with substitution of Asp, Gln, or Glu for Asn being preferred. Known procedures for inactivating N-glycosylation sites in proteins include those described in U.S. Pat. No. 5,071,972 and EP 276,846.

Other variants are prepared by modifying KEX2 protease processing sites in the mature protein to enhance expression of the desired protein in yeast cells in which KEX2 protease activity is present. The adjacent basic residue pairs that constitute KEX2 protease processing sites, and are to be inactivated by adding, substituting or deleting residue(s), are Arg-Arg, Arg-Lys, and Lys-Arg pairs. Lys-Lys pairs are considerably less susceptible to KEX2 cleavage, and conversion of Arg-Arg, Arg-Lys, and Lys-Arg pairs to a Lys-Lys doublet is a conservative and preferred alteration that essentially inactivates the KEX2 sites. EP212,914 discloses the use of site-specific mutagenesis to inactivate KEX2 protease sites in a protein.

The heterologous proteins may comprise polypeptides added to facilitate purification and identification (e.g., the antigenic identification peptides described in U.S. Pat. No. 5,011,912 and Hopp et al., *Bio/Technology* 6:1204, 1988; or a poly-His peptide). One such peptide is the FLAG® peptide DYKDDDDK (SEQ ID NO:12) which is a highly antigenic sequence that provides an epitope reversibly bound by a specific monoclonal antibody (e.g., the monoclonal antibody produced by the hybridoma designated 4E11 and deposited with the American Type Culture Collection under accession no. HB 9259) to enable rapid assay and facilitate purification of the expressed recombinant polypeptide fused thereto. The FLAG® peptide is cleaved by bovine mucosal enterokinase at the residue immediately following the Asp-Lys pairing. DNA encoding the FLAG® peptide, if present, should be positioned between the DNA encoding the signal peptide and the DNA encoding the heterologous protein.

Recombinant expression vectors encoding a heterologous protein are transfected into yeast host cells by conventional techniques. The transfected cells are cultivated under conditions suitable to effect expression of the desired recombinant protein, which is purified from the cells or culture medium, depending on the nature of the expression system and the expressed protein (e.g., whether the protein is fused to a signal peptide and whether the protein is soluble or membrane-bound). As will be understood by the skilled artisan, cultivation conditions will vary according to factors that include the type of host cell and particular expression vector employed.

Yeast transformation protocols are known to those of skill in the art. One such protocol is described by Hinnen et al., *Proc. Natl. Acad. Sci. USA* 75:1929 (1978). The Hinnen et al. protocol selects for Trp$^+$transformants in a selective medium consisting of 0.67% yeast nitrogen base, 0.5% casamino acids, 2% glucose, 10 µg/ml adenine and 20 µg/ml uracil.

Yeast host cells transformed by vectors containing ADH2 promoter sequence may be cultivated in a "rich" medium. An example of a rich medium is one consisting of 1% yeast extract, 2% peptone, and 1% glucose supplemented with 80 µg/ml adenine and 80 µg/ml uracil. Derepression of the ADH2 promoter occurs when glucose is exhausted from the medium.

Recombinant polypeptides secreted from yeast cells can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column. If the heterologous protein is not secreted, the yeast cells can be disrupted by any convenient method, including freeze-thaw cycling, sonication, mechanical disruption, or use of cell lysing agents.

Affinity chromatography may be employed in the purification process. A receptor protein (or the extracellular domain thereof) may be attached to a solid support material by standard procedures for use in purifying the cognate ligand protein, and vice versa. Immunoaffinity columns comprising an antibody that binds the desired protein also may be employed.

In one purification procedure, the desired protein is concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion or cation exchange resin can be employed. Finally, one or more reverse-phase high performance liquid chromatography (RP-HPLC) steps employing hydrophobic RP-HPLC media, (e.g., silica gel having pendant methyl or other aliphatic groups) can be carried out. Some or all of the foregoing purification steps, in various combinations, may be employed to provide a substantially homogeneous recombinant protein.

The following examples are for the purposes of illustrating certain embodiments of the invention, and are not to be construed as limiting the scope of the invention as claimed herein.

EXAMPLE 1

Isolation of Mutant *S. cerevisiae* Strain ATCC74224

A novel mutant yeast strain was generated and isolated as follows. The procedures are generally as described in Rose et al., *Methods in Yeast Genetics, A Laboratory Course Manual*, Cold Spring Harbor Press, Cold Spring Harbor, N.Y., 1990, at pages 13–15.

S. cerevisiae strain XV617-1-3B [a, his6, leu2-1, trpl-1, ura3, ste5] was obtained from the University of Washington, Department of Genetics Yeast Strain Bank, Seattle, Wash. A fresh overnight culture of XV617-1-3B transformed with a recombinant expression vector was grown in YEPG (1% yeast extract, 2% peptone, 2% glucose) to a cell density of about $1-2\times10^8$ cells/ml. The vector encoded a reporter protein that is not well-secreted from this strain. The culture was diluted to $5\times10^7$ cells/ml in $KH_2PO_4$, pH 7.0, 10 mls total volume. 0.45 ml of the mutagen ethylmethane sulfonate (EMS, available from Sigma Chemical Co., St. Louis, Missouri) was added, and the culture was incubated at 30° C. for 30 minutes. Cells were then plated at a density of 500–1000 cells/plate on YNB ⁻trp medium (0.67% yeast nitrogen base, 2% glucose, amino acids minus tryptophan at approximately 20 µg/ml).

Colonies were screened for secretion of the reporter protein using an antibody immunoreactive with the reporter protein. Positive colonies were detected by binding of the antibody to secreted product on nitrocellulose filters. A mutant isolated from this screening process was designated YIMX1. Strain YIMX1 was crossed to strain X2181-1B [a, trpl-1, gall, adel, his2], obtained from the Yeast Genetic Stock Center, University of California, Berkeley, Calif., to create the diploid strain designated YIMX2. This diploid is heterozygous at the mutant locus (an unidentified locus that allows improved secretion of the reporter protein). The mutation of interest was shown to be recessive in that strain YIMX2 did not exhibit the property of better secretion of the reporter protein. For this reason, UV mutagenesis was performed on YIMX2 to induce homozygosis at the mutant locus (a crossing-over event that would result in information from one chromosome replacing that on the homologous chromosome).

YIMX2 was transformed with the reporter-encoding expression vector employed in the first mutagenesis procedure. The UV source was a Stratalinker® UV Crosslinker (Stratagene Cloning Systems, LaJolla, Calif., which emits about 0.67 mjoules per second. YNB ⁻trp plates spread with $0.5-1\times10^3$ colonies per plate were irradiated for 12–15 seconds. Colonies were screened as above for increased secretion of the reporter protein. A strain demonstrating increased secretion of the reporter protein was isolated and designated YIMX-9.

A sample of the isolated mutant strain *S. cerevisiae* YIMX-9 was deposited with the American Type Culture Collection in Rockville, Md., on May 4, 1993, and assigned accession number ATCC 74224. The deposit was made under the terms of the Budapest Treaty.

EXAMPLE 2

Expression of a Recombinant Fusion Protein in Mutant Strain ATCC 74224

A recombinant fusion protein comprising GM-CSF and IL-3 joined by a peptide linker was expressed in the mutant *Saccharomyces cerevisiae* strain ATCC 74224 produced in example 1. Two different expression vectors were constructed, the first encoding a leader derived from the yeast alpha factor prepro peptide, fused to the GM-CSF/IL-3 fusion protein. The second expression vector encoded a signal peptide of the present invention (derived from murine type I IL-1 receptor) fused to the GM-CSF/IL-3 fusion protein.

The fusion protein encoded by the expression vectors is huGM-CSF/Gly$_4$SerGly$_5$Ser (SEQ ID NO: 13)/huIL-3, as described in U.S. Pat. No. 5,073,627, hereby incorporated by reference. The GM-CSF component (termed the "variant GM-CSF" elsewhere in this example) is a human GM-CSF protein differing from a native human GM-CSF protein in that the amino acid at position 23 of the native sequence has been changed from Arg to Leu. This amino acid substitution inactivates a KEX2 protease cleavage site found in the native protein, thus rendering the variant protein less susceptible to proteolysis by the KEX2 protease in yeast cells. In addition, amino acid 27 has been changed from Asn to Asp, and amino acid 39 has been changed from Thr to Glu, to inactivate two N-glycosylation sites. Inactivation of KEX2 cleavage sites and N-glycosylation sites in proteins in general was discussed above.

The Gly$_4$SerGly$_5$Ser (SEQ ID NO: 13) sequence is a peptide linker. The IL-3 component is a human IL-3 protein differing from a native human IL-3 protein in that amino acids 15 and 70 were each changed from Asn to Asp to inactivate two N-glycosylation sites. The amino acid at position 8 is Pro, as opposed to the Ser at position 8 that has been reported for an allelic variant of human IL-3.

The expression vector encoding the yeast α-factor leader sequence fused to the N-terminus of the huGM-CSF/Gly$_4$SerGly$_5$Ser (SEQ ID NO: 13)/huIL protein is designated pIXY321. Construction of the pIXY321 vector is described in U.S. Pat. No. 5,073,627. The pIXY321 vector comprises the yeast alcohol dehydrogenase II (ADH2) promoter operably linked to DNA encoding a yeast α-factor leader peptide. The leader comprises amino acids 1–85 of the yeast α-factor prepro sequence presented in FIG. 1A of U.S. Pat. No. 4,546,082 (hereby incorporated by reference), except that a mutation replaces the Ser at position 81 with Pro. The leader thus comprises the α-factor pre region (signal peptide) and the pro region through the LysArg residues that constitute a KEX2 protease processing site. DNA encoding the GM-CSF/IL-3 fusion protein is fused in the same reading frame to the 3' end of the leader-encoding DNA. The vector contains an F1 origin of replication and an origin of replication derived from pBR322, both functional in *E.coli*, and a 2u origin of replication functional in yeast. Selective markers include an ampicillin resistance gene (for selection in *E.coli*) and Trp1 for selection in yeast.

A second expression vector, encoding a signal peptide of the present invention fused to the N-terminus of the above-described GM-CSF/IL-3 fusion protein, was constructed as follows. A recombinant vector designated pIXY224 comprises vector backbone sequences identical to those described for pIXY321 above, and contains a *K. lactis* K1 signal sequence fused to DNA encoding huGM-CSF [Leu$^{23}$Asp$^{27}$Glu$^{39}$]. pIXY224 was digested with XhoI (which cleaves downstream of the ADH2 promoter and upstream of the K1 signal sequence) and with Bgl2 (which cleaves in the variant GM-CSF sequence near the 5' end thereof). The large fragment containing the vector sequences and most of the GM-CSF-encoding sequence was isolated. Synthetic oligonucleotides were annealed and ligated into the vector fragment to regenerate the 5' end of the huGM-CSF[Leu$^{23}$Asp$^{27}$Glu$^{39}$]-encoding DNA and fuse a sequence encoding a signal peptide of the present invention to the 5' end of the variant GM-CSF sequence. *E. coli* cells were transformed with the ligation mixture and the desired recombinant vector, designated pIXY239, was isolated.

pIXY239 was digested with Bgl2 and SpeI, and the large fragment containing vector sequences, the promoter, signal sequence and 5' end of the variant GM-CSF sequence was isolated. A Bgl2/SpeI fragment isolated from pIXY321 (described above) was ligated into the vector fragment. This pIXY321 Bgl2/SpeI fragment contains the remainder of the variant GM-CSF sequence followed by a peptide linker, followed by the huIL-3[Pro$^8$Asp$^{15}$Asp$^{70}$]-encoding sequence, as described above. E. coli cells were transformed with the ligation mixture, and the desired recombinant vector, designated pIXY654, was isolated. pIXY654 thus comprises the yeast ADH2 promoter operably linked to a signal sequence positioned immediately upstream of (and in the same reading frame as) the huGM-CSF/Gly$_4$SerGly$_5$Ser (SEQ ID NO: 13)/huIL-3-encoding sequence.

The vector encodes the following signal peptide of the present invention:

(SEQ ID NO: 3)

MetLysValLeuLeuGlyLeuIleCysLeuMetValLeuGlyThrAlaLeuAla

The underlined segment is a murine type I IL-1R signal peptide lacking the last (C-terminal) four amino acids thereof. The native signal peptidase recognition site thus has been deleted from the IL-1R signal sequence and replaced with the AlaLeuAla signal peptidase recognition site shown at the −3 to −1 positions. The double-underlined segment is a spacer peptide that is encoded by a linker containing Ban1 and Asp718 restriction sites. These restriction sites may be employed for such purposes as replacing the murine IL-1R-derived signal sequence with a different mammalian signal sequence lacking its native signal peptidase recognition site. pIXY654 is identical to pIXY321 constructed above except for the signal sequence fused to the N-terminus of the GM-CSF/IL-3 fusion protein.

S. cerevisiae mutant strain YIMX-9 (ATCC 74224) cells were transformed by conventional techniques with either pIXY321 or pIXY654, as was YIMX-8 (a mutant S. cerevisiae strain that was isolated during the same mutation procedure used to produce strain YIMX-9 in example 1). An S. cerevisiae strain designated XV2181 also was transformed with the two vectors. XV2181, a diploid S. cerevisiae strain, was formed by mating the above-described strains XV617-1-3B and X2181-1B.

The transformed cells were cultured in 10 ml shake flasks in 1% yeast extract, 2% peptone, and 1% glucose supplemented with 80 μg/ml adenine and 80 μg/ml uracil. Derepression of the ADH2 promoter occurs when glucose is exhausted from the medium. After cultivation for about 24–28 hours to permit expression and secretion of the soluble fusion protein into the supernatant, the cells were pelleted by centrifugation and the supernatant (culture medium) was filtered. The filtered supernatant was analyzed for the GM-CSF/IL-3 fusion protein in a conventional ELISA assay.

FIG. 1 presents the results, in terms of the μg/ml of the recombinant fusion protein produced by the various cell cultures after cultivation for 24–28 hours. As is evident from FIG. 1, higher levels of the above-described GM-CSF/IL-3 fusion protein were secreted into the supernatant of transformed YIMX-9 cell cultures than from supernatants of the other two transformed strains (XV2181 or the "sibling" mutant strain YIMX-8). This was true for cells transformed with either of the two expression vectors, which differed only in the signal peptide (modified murine typeI IL-1R-AlaLeuAla signal peptide or yeast α-factor prepro leader) attached to the N-terminus of the GM-CSF/IL-3 fusion protein when initially expressed.

Figure 2:
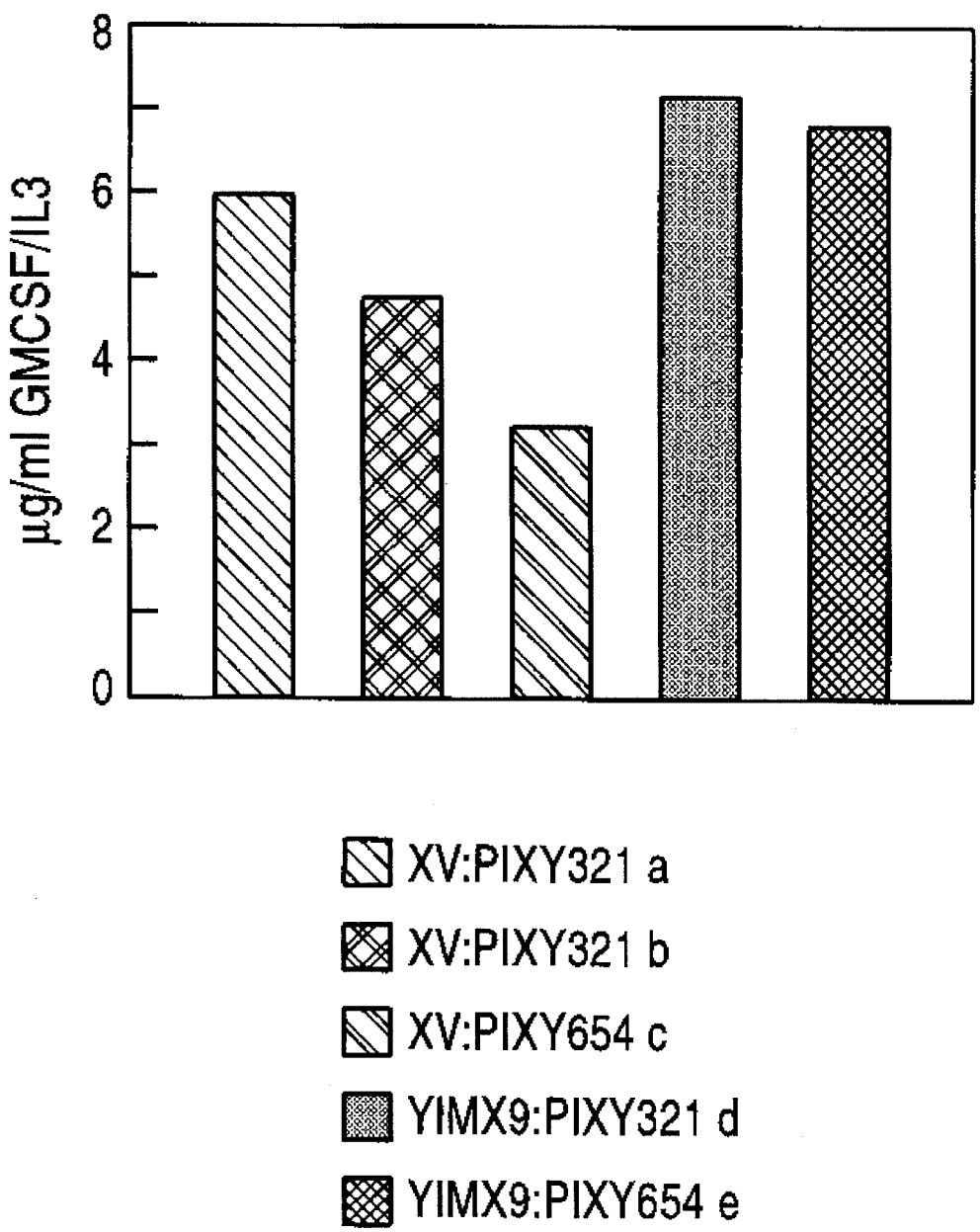
FIG. 2 presents the results of a second experiment described in example 2, in which levels of secretion of a heterologous fusion protein were compared for two yeast strains (including the novel mutant yeast strain designated YIMX9) transformed with two different expression vectors. One of the vectors, pIXY654, is an expression vector of the present invention, encoding a novel signal peptide.

FIG. 2 presents the results of a second experiment comparing levels of production of the above-described GM-CSF/IL-3 fusion protein in mutant strain YIMX9 and in the XV2181 strain. Both strains were transformed with pIXY321 or pIXY654, cultivated in 10 ml shake flasks for 24–28 hours, and the amount of GM-CSF/IL-3 fusion protein in each culture supernatant was determined as described above. Bar "a" in FIG. 2 represents the amount of the desired protein in the supernatant of a culture of strain XV2181 transformed with the pIXY321 expression vector comprising the yeast α-factor signal peptide. Bar "b" represents a second culture of XV2181 transformed with pIXY321. Bar "c" represents XV2181 transformed with the pIXY654 expression vector containing the novel signal peptide derived from IL-1R. Bar "d" represents YIMX9 transformed with pIXY321. Bar "e" represents YIMX9 transformed with pIXY654.

The data of FIGS. 1 and 2 demonstrate that the novel yeast strain of the present invention is useful as a host strain for production of recombinant proteins. In addition, the effectiveness of the murine IL-1R-derived signal peptide of the present invention as an alternative to yeast signal peptides in expressing recombinant proteins in yeast host cells was demonstrated. The recombinant protein was effectively secreted from each of the three cell lines transformed with the vector comprising the IL-1R-derived signal sequence, and was secreted at levels comparable to those achieved with the yeast α-factor-derived leader when the mutant strain YIMX9 was employed.

EXAMPLE 3

Expression of a T-cell Growth Factor in Mutant Strain ATCC 74224

Two expression vectors encoding a human T-cell growth factor (TCGF) were constructed. The vectors comprise the ADH2 promoter, and the vector backbone sequences are as described above for pIXY321. One vector encodes the TCGF fused to its native signal sequence, an unusually long (48-amino acid) signal peptide. This human TCGF protein, as well as DNA encoding the protein (cloned from epithelial cells), are described in co-pending U.S. application Ser. No. 08/31,399 and PCT application WO 95/27722, hereby incorporated by reference. The other vector encodes the TCGF fused to the C-terminus of the murine IL-1R-derived signal peptide of the present invention having the amino acid sequence:

MetLysValLeuLeuGlyLeuIleCysLeuMetValLeuGlyThrAlaLeuAla. (SEQ ID NO: 3)

Figure 3:
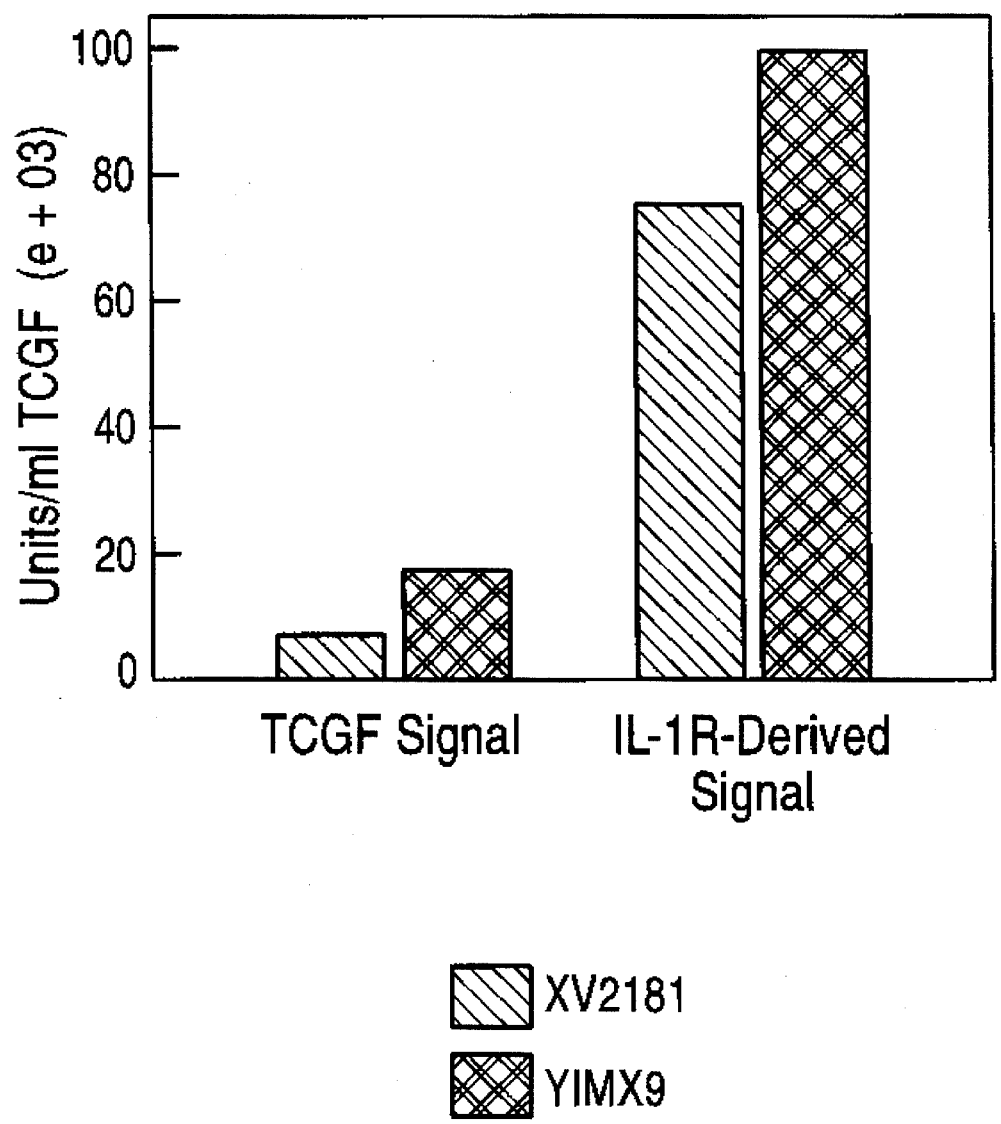
FIG. 3 presents the results of the experiment described in example 3, in which levels of secretion of a T-cell growth factor protein (TCGF) were compared for two yeast strains (including the novel mutant yeast strain designated YIMX9) transformed with two different expression vectors. One vector comprises a novel signal peptide of the present invention and the other comprises the native TCGF signal peptide.

The above-described yeast strain XV2181 and the mutant strain YIMX9 were each transformed with the vectors and cultivated by procedures described in example 2. Culture supernatants were analyzed for the presence of the TCGF protein, and the results are presented in FIG. 3. The TCGF protein was secreted at higher levels from both strains when the novel IL-1R-derived signal peptide was employed, compared to the native TCGF signal peptide. In addition, higher levels of TCGF were secreted from YIMX9 than from XV2181, for both expression vectors.

In another study, an expression vector similar to pIXY321 but containing TCGF-encoding DNA in place of the GM-CSF/IL-3-encoding gene fusion was constructed.

YIMX9 and XV2181 were transformed with the expression vector (encoding TCGF DNA fused to the α-factor leader) and cultivated by procedures described above. YIMX9 proved to be a useful host cell for this expression vector. The TCGF protein was secreted into the culture supernatant at a similar level from the XV2181 and YIMX9 strains, which level was about 10 times higher than that achieved using the murine IL-1R-derived signal.

---

What is claimed is:

1. An expression vector comprising a yeast promoter operably linked to a DNA segment encoding a signal peptide, wherein said signal peptide comprises an amino acid sequence selected from the group consisting of:

MetLysValLeuLeuGlyLeuIle-        (SEQ ID NO:1)
    -CysLeuMetVal(Pro)$_m$(Z)$_n$AlaXAla,

MetGluAsnMetLysValLeuLeuGlyLeuIle-    (SEQ ID NO:2)
    -CysLeuMetVal(Pro)$_m$(Z)$_n$AlaXAla, and MetLysValLeuLeuArgLeuIle-        (SEQ ID NO:5)
    -CysPheIleAlaLeuLeu(Z)$_n$AlaXAla, wherein:

m is 0 or 1,

Z represents a spacer peptide comprising from 1–5 amino acids, n is 0 or 1, and

X is an amino acid selected from the group consisting of Leu, Phe, and Gln.

2. A vector of claim 1, wherein X is Leu.

3. A vector of claim 2, wherein said signal peptide comprises the amino acid sequence:

MetLysValLeuLeuGlyLeuIleCysLeuMetValLeuGlyThrAlaLeuAla.    (SEQ ID NO: 3)

4. An expression vector of claim 1, further comprising a DNA encoding a heterologous protein, fused to the 3' end of said DNA segment encoding the signal peptide.

5. An expression vector of claim 4 wherein said heterologous protein is selected from the group consisting of cytokines, cytokine receptors, fusion proteins comprising two or more cytokines, and fusion proteins comprising two or more cytokine receptors.

6. A vector of claim 5 wherein said heterologous protein is a cytokine receptor selected from the group consisting of interleukin receptors, colony stimulating factor receptors, and tumor necrosis factor receptors.

7. A vector of claim 5 wherein said heterologous protein is a cytokine selected from the group consisting of interleukins, interferons, colony stimulating factors, and tumor necrosis factors.

8. An expression vector of claim 5 wherein said heterologous protein is a fusion protein comprising GM-CSF and interleukin-3, and said signal peptide comprises the amino acid sequence:

MetLysValLeuLeuGlyLeuIleCysLeuMetValLeuGlyThrAlaLeuAla. (SEQ ID NO: 3)

9. A yeast cell transformed with an expression vector of claim 4.

10. A yeast cell transformed with an expression vector of claim 5.

11. A yeast cell transformed with an expression vector of claim 8.

MetLysValLeuLeuGlyLeuIleCysLeuMetVal(Pro)$_m$(Z)$_n$AlaXAla, (SEQ ID NO: 1)

MetGluAsnMetLysValLeuLeuGlyLeuIleCysLeuMetVal(Pro)$_m$(Z)$_n$AlaXAla, and (SEQ ID NO: 2)

MetLysValLeuLeuArgLeuIleCysPheIleAlaLeuLeu(Z)$_n$AlaXAla, (SEQ ID NO: 5)

12. A process for preparing a recombinant heterologous protein, comprising culturing a transformed cell of claim 9 under conditions that promote expression of said protein, and purifying the protein from the culture medium.

13. A process for preparing a recombinant heterologous protein, comprising culturing a transformed cell of claim 10 under conditions that promote expression of said protein, and purifying the protein from the culture medium.

14. A process for preparing a recombinant heterologous protein, comprising culturing a transformed cell of claim 11 under conditions that promote expression of said protein, and purifying the protein from the culture medium.

15. A process according to claim 12, wherein said cell is of *S. cerevisiae* strain ATCC 74224.

16. A process according to claim 13, wherein said cell is of *S. cerevisiae* strain ATCC 74224.

17. A process according to claim 14, wherein said cell is of *S. cerevisiae* strain ATCC 74224.

18. An expression vector comprising a yeast promoter operably linked to DNA encoding a signal peptide consisting of the amino acid sequence:

MetLysValLeuLeuGlyLeuIle-CysLeuMetValLeuGlyThrAlaLeuAla (SEQ ID NO:3) fused to the N-terminus of a fusion protein comprising GM-CSF and interleukin-3.

19. A yeast cell of *S. cerevisiae* strain ATCC 74224 transformed with an expression vector of claim 18.

20. A DNA sequence comprising a yeast promoter operably linked to DNA encoding a signal peptide comprising an amino acid sequence selected from the group consisting of:

wherein Z represents a spacer peptide comprising from 1–5 amino acids, m is 0 or 1, n is 0 or 1, and X is an amino acid selected from the group consisting of Leu, Phe, and Gln.

21. A DNA sequence of claim 20, wherein said signal peptide comprises the amino acid sequence MetLysValLeuLeuGlyLeuIleCysLeuMetValleuGlyThrAlaLeuAla.

22. A yeast cell of *S. cerevisiae* strain ATCC 74224 transformed with an expression vector according to claim 4.

23. A transformed cell of claim 22 wherein said expression vector encodes a signal peptide comprising the amino acid sequence:

(SEQ ID NO: 3)
MetLysValLeuLeuGlyLeuIleCysLeuMetValLeuGlyThrAlaLeuAla

24. A vector of claim 5 wherein said heterologous protein is a fusion protein comprising two or more cytokines selected from the group consisting of interleukins, interferons, colony stimulating factors, and tumor necrosis factors.

25. A vector of claim 5 wherein said heterologous protein is a fusion protein comprising two or more cytokine receptors selected from the group consisting of interleukin receptors, colony stimulating factor receptors, and tumor necrosis factor receptors.

\* \* \* \* \*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 17 amino acids
( B ) TYPE: amino acid
( C ) STRANDEDNESS:
( D ) TOPOLOGY: linear ( i i ) MOLECULE TYPE: protein ( i i i ) HYPOTHETICAL: NO ( i v ) ANTI-SENSE:

( x i ) SEQUENCE DESCRIPTION: SEQ ID NO:1:

Met Lys Val Leu Leu Gly Leu Ile Cys Leu Met Val Pro Xaa Ala Xaa
1               5                   10                  15

Ala ( 2 ) INFORMATION FOR SEQ ID NO:2:

( i ) SEQUENCE CHARACTERISTICS:
( A ) LENGTH: 20 amino acids
( B ) TYPE: amino acid
( C ) STRANDEDNESS:
( D ) TOPOLOGY: linear ( i i ) MOLECULE TYPE: protein ( i i i ) HYPOTHETICAL: NO ( i v ) ANTI-SENSE:

( x i ) SEQUENCE DESCRIPTION: SEQ ID NO:2:

Met Glu Asn Met Lys Val Leu Leu Gly Leu Ile Cys Leu Met Val Pro
1               5                   10                  15

Xaa Ala Xaa Ala
            20

( 2 ) INFORMATION FOR SEQ ID NO:3:

( i ) SEQUENCE CHARACTERISTICS:
( A ) LENGTH: 18 amino acids
( B ) TYPE: amino acid
( C ) STRANDEDNESS:
( D ) TOPOLOGY: linear ( i i ) MOLECULE TYPE: protein ( i i i ) HYPOTHETICAL: NO ( i v ) ANTI-SENSE:

( x i ) SEQUENCE DESCRIPTION: SEQ ID NO:3:

Met Lys Val Leu Leu Gly Leu Ile Cys Leu Met Val Leu Gly Thr Ala
1               5                   10                  15

Leu Ala ( 2 ) INFORMATION FOR SEQ ID NO:4:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE:

( x i ) SEQUENCE DESCRIPTION: SEQ ID NO:4:

```
Met Glu Asn Met Lys Val Leu Leu Gly Leu Ile Cys Leu Met Val Leu
 1               5                  10                  15

Gly Thr Ala Leu Ala
            20
```

( 2 ) INFORMATION FOR SEQ ID NO:5:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE:

( x i ) SEQUENCE DESCRIPTION: SEQ ID NO:5:

```
Met Lys Val Leu Leu Arg Leu Ile Cys Phe Ile Ala Leu Leu Xaa Ala
 1               5                  10                  15

Xaa Ala
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE:

( x i ) SEQUENCE DESCRIPTION: SEQ ID NO:6:

```
Met Lys Val Leu Leu Arg Leu Ile Cys Phe Ile Ala Leu Leu Leu Gly
 1               5                  10                  15

Thr Ala Leu Ala
            20
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Glu Ala Glu Ala
1

( 2 ) INFORMATION FOR SEQ ID NO:8:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: N-term. mIL-1R(I)

( x i ) SEQUENCE DESCRIPTION: SEQ ID NO:8:

Met Glu Asn Met Lys Val Leu Leu Gly Leu Ile Cys Leu Met Val Pro
1               5                   10                  15

Leu Leu Ser ( 2 ) INFORMATION FOR SEQ ID NO:9:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: cDNA to mRNA ( v i i ) IMMEDIATE SOURCE:
        ( B ) CLONE: 5'mIL-1R(I)

( x i ) SEQUENCE DESCRIPTION: SEQ ID NO:9:

ATGGAGAATA TGAAAGTGCT ACTGGGGCTC ATTTGTCTCA TGGTGCCTCT GCTGTCG        57

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: N-term. hIL-1R(I)

( x i ) SEQUENCE DESCRIPTION: SEQ ID NO:10:

Met Lys Val Leu Leu Arg Leu Ile Cys Phe Ile Ala Leu Leu Ile Ser
1               5                   10                  15

Ser ( 2 ) INFORMATION FOR SEQ ID NO:11:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA to mRNA ( v i i ) IMMEDIATE SOURCE:
        ( B ) CLONE: 5'hIL-1R(I)

( x i ) SEQUENCE DESCRIPTION: SEQ ID NO:11:

ATGAAAGTGT TACTCAGACT TATTTGTTTC ATAGCTCTAC TGATTTCTTC T        51

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (iv) ANTI-SENSE: NO (vii) IMMEDIATE SOURCE:
        (B) CLONE: FLAG peptide (xi) SEQUENCE DESCRIPTION: SEQ ID NO:12:

Asp Tyr Lys Asp Asp Asp Asp Lys
1               5

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Gly Gly Gly Gly Ser Gly Gly Gly Gly Gly Ser
1             5                   10